United States Patent
McKinnon

(10) Patent No.: US 7,074,241 B2
(45) Date of Patent: Jul. 11, 2006

(54) VARIABLE GEOMETRY RIM SURFACE ACETABULAR SHELL LINER

(75) Inventor: Brian W. McKinnon, Bartlett, TN (US)

(73) Assignee: Smith & Nephew, Inc., Memphis, TN (US)

(*) Notice: Subject to any disclaimer, the term of this patent is extended or adjusted under 35 U.S.C. 154(b) by 0 days.

(21) Appl. No.: 09/808,228

(22) Filed: Mar. 14, 2001

(65) Prior Publication Data
US 2001/0032021 A1    Oct. 18, 2001

Related U.S. Application Data

(60) Provisional application No. 60/189,182, filed on Mar. 14, 2000.

(51) Int. Cl.
*A61F 2/32* (2006.01)

(52) U.S. Cl. .................. 623/22.24; 623/22.21

(58) Field of Classification Search ... 623/22.11–22.39
See application file for complete search history.

(56) References Cited

U.S. PATENT DOCUMENTS

| | | |
|---|---|---|
| 4,437,193 A | 3/1984 | Oh |
| 4,795,469 A | 1/1989 | Oh |
| 5,226,917 A | 7/1993 | Schryver |
| 5,310,408 A | 5/1994 | Schryver et al. |
| 5,314,487 A | 5/1994 | Schryver et al. |
| 5,443,519 A | 8/1995 | Averill et al. |
| 5,507,824 A * | 4/1996 | Lennox ............ 623/22.25 |
| 5,702,477 A | 12/1997 | Capello et al. |
| 5,782,928 A | 7/1998 | Ries et al. |
| 5,800,555 A | 9/1998 | Gray, III |
| 5,879,404 A * | 3/1999 | Bateman et al. ...... 623/22.21 |
| 5,904,720 A | 5/1999 | Farrar et al. |
| 5,972,032 A | 10/1999 | Lopez et al. |

FOREIGN PATENT DOCUMENTS

| | | |
|---|---|---|
| DE | 44 28 407 A1 | 2/1996 |
| EP | 0 901 777 A2 | 3/1999 |
| WO | WO 96/04866 | 2/1996 |

OTHER PUBLICATIONS

T. Cobb, et al., *The Elevated-Rim Acetabular Liner in Total Hip Arthroplasty: Relationship to Postoperative Dislocation*, Journal of Bone and Joint Surgery, vol. 78-A, No. 1, Jan. 1996, pp. 80-86.

Thornberry, et al., *The Effects of Neck Geometry and Acetabular Design on the Motion to Impingement in Total Hip Replacement*, A Scientific Exhibit at the 1998 AAOS Meeting, New Orleans, Louisiana, 1998.

(Continued)

*Primary Examiner*—Thomas Barrett
(74) *Attorney, Agent, or Firm*—Kilpatrick Stockton LLP

(57) ABSTRACT

An acetabular shell liner having a variable rim surface geometry, which improves range of motion of the femoral component within the liner and decreases the incidence of dislocation and subluxation, and methods of making and using the acetabular shell liner. Prosthetic devices, more particularly hip joint prostheses, containing the acetabular shell liner having a variable rim surface geometry are also provided.

26 Claims, 9 Drawing Sheets

LEFT HIP

OTHER PUBLICATIONS

B. McGrory, et al., *Correlation of Measured Range of Hip Motion Following Total Hip Arthroplasty and Responses to a Questionnaire*, Journal of Arthroplasty, vol. II, No. 5, 1996.

Brochure entitled "Reflection Lateralized Liners . . . Reflection Acetabular System," Smith & Nephew (May. 1997).

Brochure entitled "Reflection Interfit . . . Porous-Coated Acetabular Component," Smith & Nephew Surgical Technique, pp. 1-20 (Jan. 1999).

International Search Report in related International Application No. PCT/US01/08221.

James W. Harkess, et al., *Variations in Design of Anteverted Acetabular Liners in THR*, A Scientific Exhibit at the 2000 AAOS Meeting, Orange County, California, Mar. 15-19, 2000, publication made available at least as early as Feb. 17, 2000.

* cited by examiner

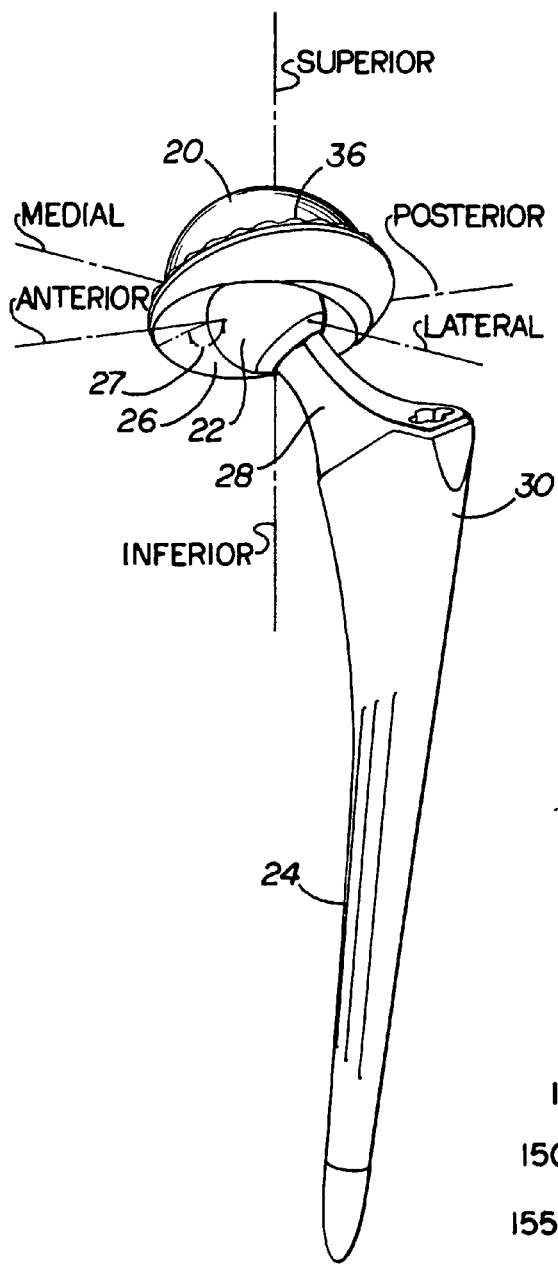
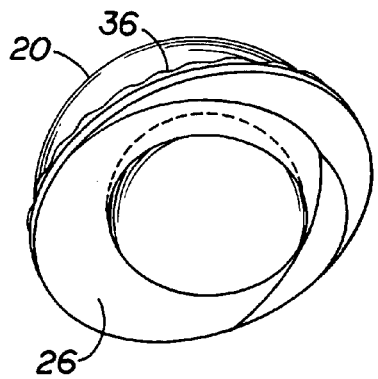
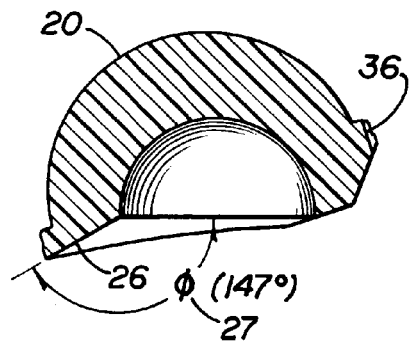
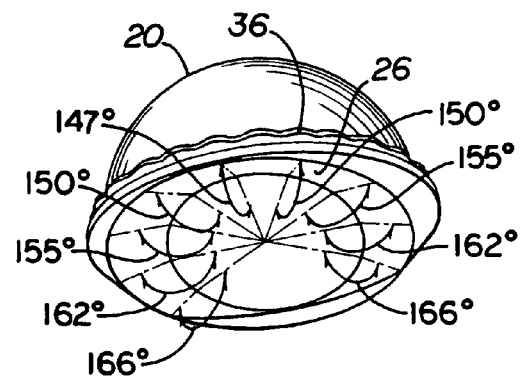
FIG 1
FIG 2A
FIG 2B
FIG 2C

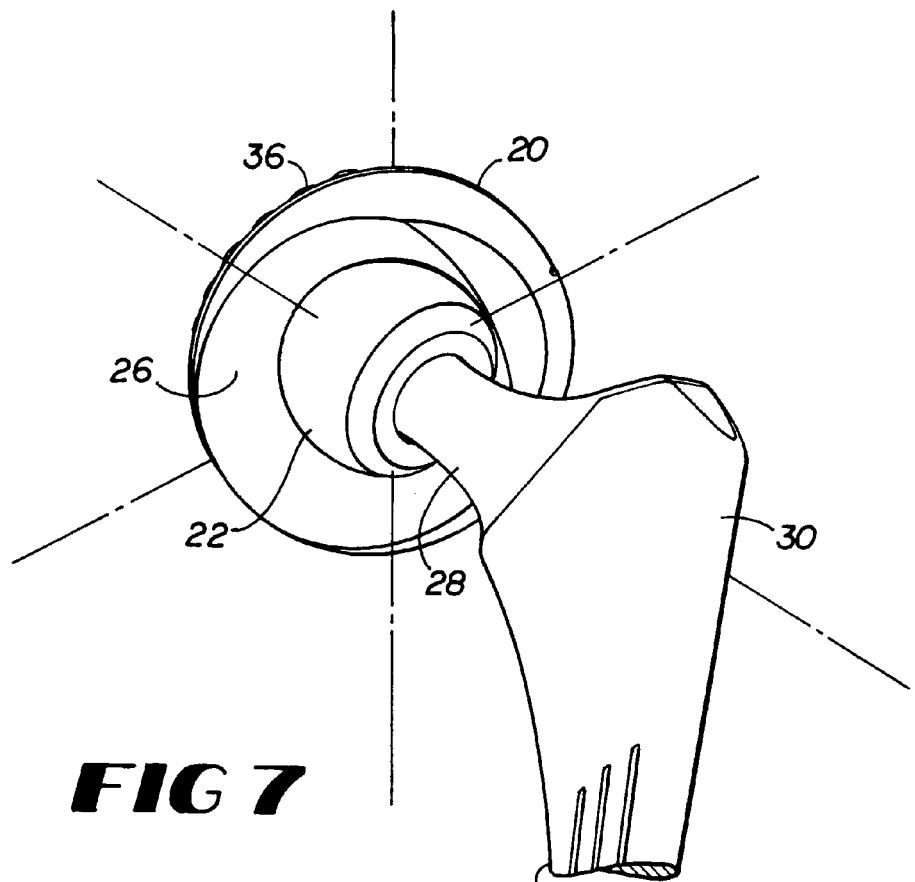
FIG 7
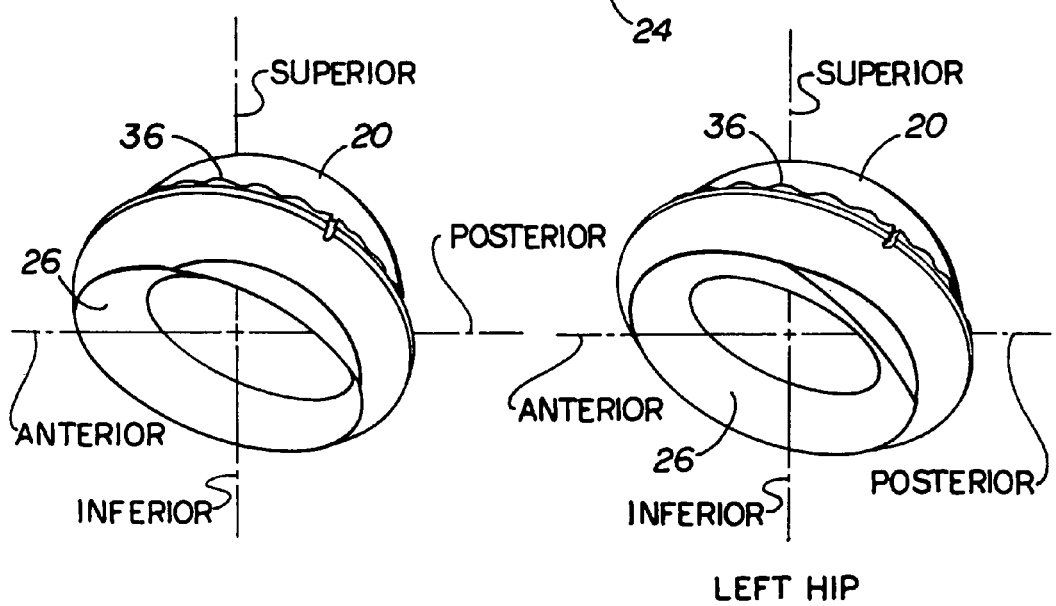
FIG 8  FIG 9

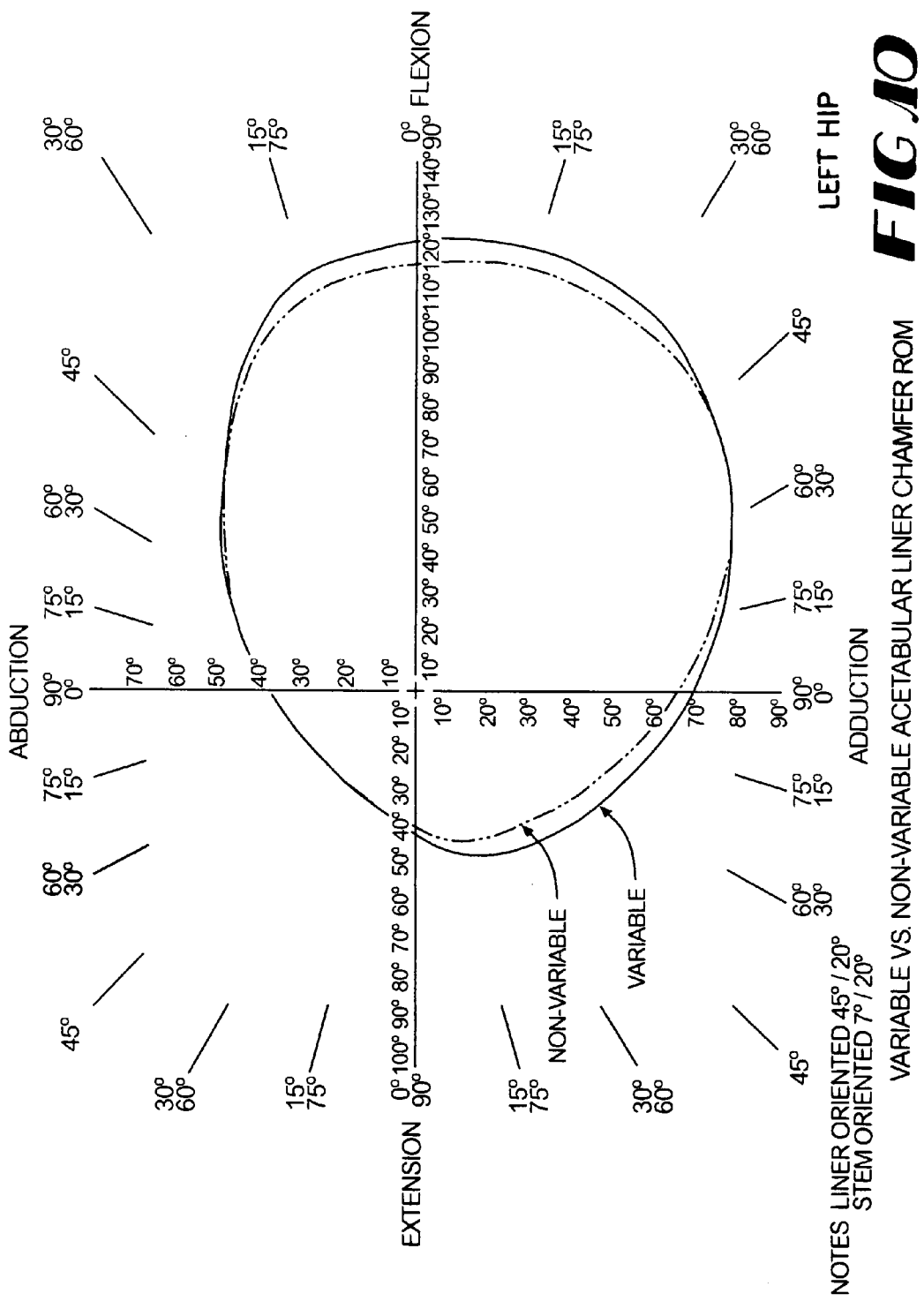

Standard configuration liner with curved impingement surface

Standard configuration liner with curved impingement surface

Liner with recessed internal diameter

VARIABLE GEOMETRY RIM SURFACE ACETABULAR SHELL LINER

This application claims the benefit of U.S. Provisional Application No. 60/189,182, filed Mar. 14, 2000.

FIELD OF THE INVENTION

This invention relates generally to acetabular prosthetic devices and more particularly to an improved acetabular shell liner wherein the liner has a variable geometry rim surface.

BACKGROUND OF THE INVENTION

Artificial implants, including hip joints, shoulder joints and knee joints, are widely used in orthopedic surgery. Hip joint prostheses are common. The human hip joint acts mechanically as a ball and socket joint, wherein the ball-shaped head of the femur is positioned within the socket-shaped acetabulum of the pelvis. In a total hip joint replacement, both the femoral head and the surface of the acetabulum are replaced with prosthetic devices.

A first general class of hip prosthetic devices included an acetabular component in which the head of a prosthetic femoral component was intended to articulate relative to the acetabular component. Initial designs included an acetabular component with a thin bearing surface, or liner, which interfaced with a large femoral component head. This design allowed for good range of motion and a low incidence of dislocation or subluxation of the femoral component head, but the thin liners proved to wear poorly, requiring replacement.

Acetabular components generally comprise an assembly of a shell and a liner, but may comprise the liner alone. Generally, a metal shell and a polymeric liner are used. However, the liner may be made of a variety of materials, including but not limited to, polyethylene, ultra high molecular weight polyethylene, and ceramic materials. The shell is usually of generally hemispherical shape and features an outer, convex surface and an inner, concave surface that is adapted to receive a polymeric shell liner. The shell liner fits inside the shell and has a convex and concave surface. The shell liner is the bearing element in the acetabular component assembly. The convex surface of the liner corresponds to the inner concave surface of the shell or acetabulum, and the liner concave surface receives the head of a femoral component.

The liner concave surface, or internal concave surface, is characterized by features relative to an axis through the center of the concave surface. This axis may or may not be aligned with the central axis of the shell. In a typical liner the concave surface has a hemispherical geometry and is also referred to as the internal diameter. In such liners, the geometry is characterized by features that are concentric to an axis that runs through the center of the internal diameter.

The acetabular component is configured to be received and fixed within the acetabulum of a pelvis. Typically, the acetabular component comprises an assembly of a shell and a liner. If only a liner is used, it is most often fixed within the acetabulum with bone cement.

The femoral component generally comprises a spherical or near-spherical head attached to an elongate stem with a neck connecting the head and stem. In use, the elongate stem is located in the intramedullary canal of the femur and the spherical or near-spherical head articulates in the liner internal diameter.

Currently, a hip joint prosthesis may comprise an acetabular component having a thicker liner and a femoral component having a smaller sized head than the initial designs. Acetabular designs that include thicker liners provide more bearing support and less surface area for wear but presents problems with dislocation and subluxation, as well as reduced range of motion, due to the smaller head size. Thus, one of the critical concerns in designing total hip joint replacement components is how to design the components to minimize contact of the neck of the femoral component with the rim of the liner during articulation, thus reducing rim contact-induced subluxation, dislocation, and wear, while allowing a maximum desired range of motion. There are a variety of acetabular liners available for use in hip replacement procedures that seek to address the issues of limited range of motion, rim-contact wear, and dislocation or subluxation.

For example, the standard, non-anteverted liner, also called a flat or zero degree liner, has a wide rim, or impingement, surface. Typically, the center of rotation of the femoral head on a standard liner is concentric with the acetabular shell. This type of standard liner is used to provide a broad range of motion. Use of this liner requires optimal positioning of the acetabular component in the acetabulum in order to provide the required range of movement for a patient. While standard liners allow a broad range of motion, if malpositioned, they present an increased possibility of dislocation. To address this problem, a high wall liner may be used.

In contrast to standard liners, high wall liners, also known as shouldered or lipped liners, employ an extended, elevated portion over a segment of the periphery of the liner internal diameter in order to increase coverage of the femoral head and thus reduce the likelihood of dislocation and aid in reduction of the head should subluxation occur. The use of high wall liners may be beneficial in cases of tenuous stability in order to avoid dislocation. See e.g. T. Cobb, et al., *The Elevated-Rim Acetabular Liner in Total Hip Arthroplasty: Relationship to Postoperative Dislocation*, Journal of Bone and Joint Surgery, Vol. 78-A, No. 1, January 1996, pp. 80–86. However, high wall liners of all designs have a reduction in the arc of motion to contact in the direction of the elevated rim segment without a corresponding increase in motion in the opposing direction. Thus, there is a substantial loss of overall range of motion compared to a standard liner. This reduction in range of motion makes the rotational positioning or clocking of these designs in the acetabulum particularly important in order to reduce rim contact with the neck of the articulating femoral component and potential acceleration of polyethylene wear at the rim as a result of this contact.

In general, anteverted liners re-orient the central axis of the internal diameter of the liner relative to the central axis of the shell. Anteverted liners shift the capture area on the head of the femoral component in order to improve hip joint stability and decrease the risk of dislocation. However, use of an anteverted liner may reduce allowed range of motion.

Some liners have a constant geometry relieved rim surface around the circumference of the internal diameter of the acetabular liner. While a relieved rim surface increases range of motion, the constant geometry may not optimize the possible range of motion because it may not be correlated to the cross-section of the femoral component during a condition of femoral component neck-liner contact. At this point the femoral component is said to be in an impingement condition with the liner.

Prosthesis range of motion has been evaluated in the past by creating a cone that defines the limits of motion to contact, or impingement angles, for the prosthesis, as described in Thornberry, et al., *The Effects of Neck Geometry and Acetabular Design on the Motion to Impingement in Total Hip Replacement*, A Scientific Exhibit at the 1998 AAOS Meeting, New Orleans, La., 1998, the entire contents of which are hereby incorporated by reference. The size of the cone depends on the design of the components. Varying the orientation of the components allows a surgeon to shift the direction of the cone. In a successful component placement, the cone is positioned so that adequate range of motion for the patient is provided. The base of the cone provides information for flexion, extension, adduction, and abduction. The direction of flexion-extension, as well as abduction-adduction, can be drawn as a line on the base of the cone. The point where the line intersects the cone is the maximum motion of prosthesis in the respective direction. Designs that provide adequate range of motion generally correlate with good clinical results. See e.g. B. McGrory, et al., *Correlation of Measured Range of Hip Motion Following Total Hip Arthroplasty and Responses to a Questionnaire*, Journal of Arthroplasty, Vol. II, No. 5, 1996.

Thus, there is a need for a method of forming an acetabular shell liner that provides optimization of the maximum range of motion and minimum interference with the femoral component neck. There is also a need for a liner formed by such a method.

SUMMARY OF THE INVENTION

Methods and structures according to this invention include a method of producing an acetabular liner in which the rim surface geometry varies, rather than being set, in order to optimize the range of motion and minimize interference with the neck of the femoral component. This variable geometry rim surface is employed around the edge of the internal concave surface of the liner, i.e. around the circumference of a generally hemispheric acetabular liner inside diameter, and allows for delayed interference, or impingement, with the neck or stem portion of the femoral component, resulting in an increased range of motion. Thus, this variable geometry rim surface delays when the neck of the femoral component contacts the rim surface of the liner during articulation, allowing an increase in the range of motion of the femoral component and optimization of the liner.

Increasing the range of motion has many benefits and advantages. For example, increasing the range of motion allows a patient a greater range of movement. Second, an increase in the range of motion provides the surgeon with greater room for error in component positioning, or clocking, during surgery. Since it is not currently possible to accurately measure the precise angle required for implantation of an acetabular component in a particular patient, it is difficult to place an implant at precisely the correct angle. A surgeon generally relies on personal experience in making this assessment. While a locking mechanism, such as a spline interface between the liner and the shell, is beneficial because it allows for multiple reorientations of the liner, fine tuning the positioning of the acetabular component during the intraoperative assessment of range of motion and stability is difficult and often imprecise. Surgeons will benefit from a wider range, or larger target area for acetabular component orientation provided by the increased range of motion.

Third, a broader range of motion decreases the likelihood of dislocation or subluxation, as it is less likely the femoral component will contact the rim of the liner and lever out of the internal concave surface of the acetabular component. Finally, a broader range of motion aids in preventing wear on the liner or shell. If a femoral component regularly contacts the rim surface of the liner, the liner will wear, releasing polyethylene debris. This debris may cause osteolysis when it escapes into nearby bone and tissue, which may lead to aseptic loosening of the implant. Additionally, if the liner wears thin, the neck of the femoral component may contact the metal shell, resulting in fatigue to the metal that may cause the neck or shell to break, or metal debris to be released into nearby bone and tissue.

These and further advantages of the present invention will become apparent after a review of the following detailed description of the disclosed embodiments.

BRIEF DESCRIPTION OF THE DRAWINGS

FIG. 1 is a perspective view of a femoral component and acetabular shell liner of a hip prosthesis for a left hip according to an embodiment of the invention.

FIG. 2A is a perspective view of a variable geometry rim surface acetabular shell liner according to an embodiment of the invention.

FIG. 2B is a cross-sectional view of the liner of FIG. 2A.

FIG. 2C illustrates the rim angle variation of the liner of FIG. 2A.

FIG. 7 is a partial view of the femoral component and acetabular shell liner of FIG. 6.

FIGS. 8 and 9 are perspective views of an acetabular shell liner according to an embodiment of the invention.

FIG. 10 is a graph showing a range of motion envelope for a variable geometry rim surface acetabular shell liner according to this invention and a range of motion envelope of a non-variable geometry rim surface liner.

DETAILED DESCRIPTION

Figures 3, 4:
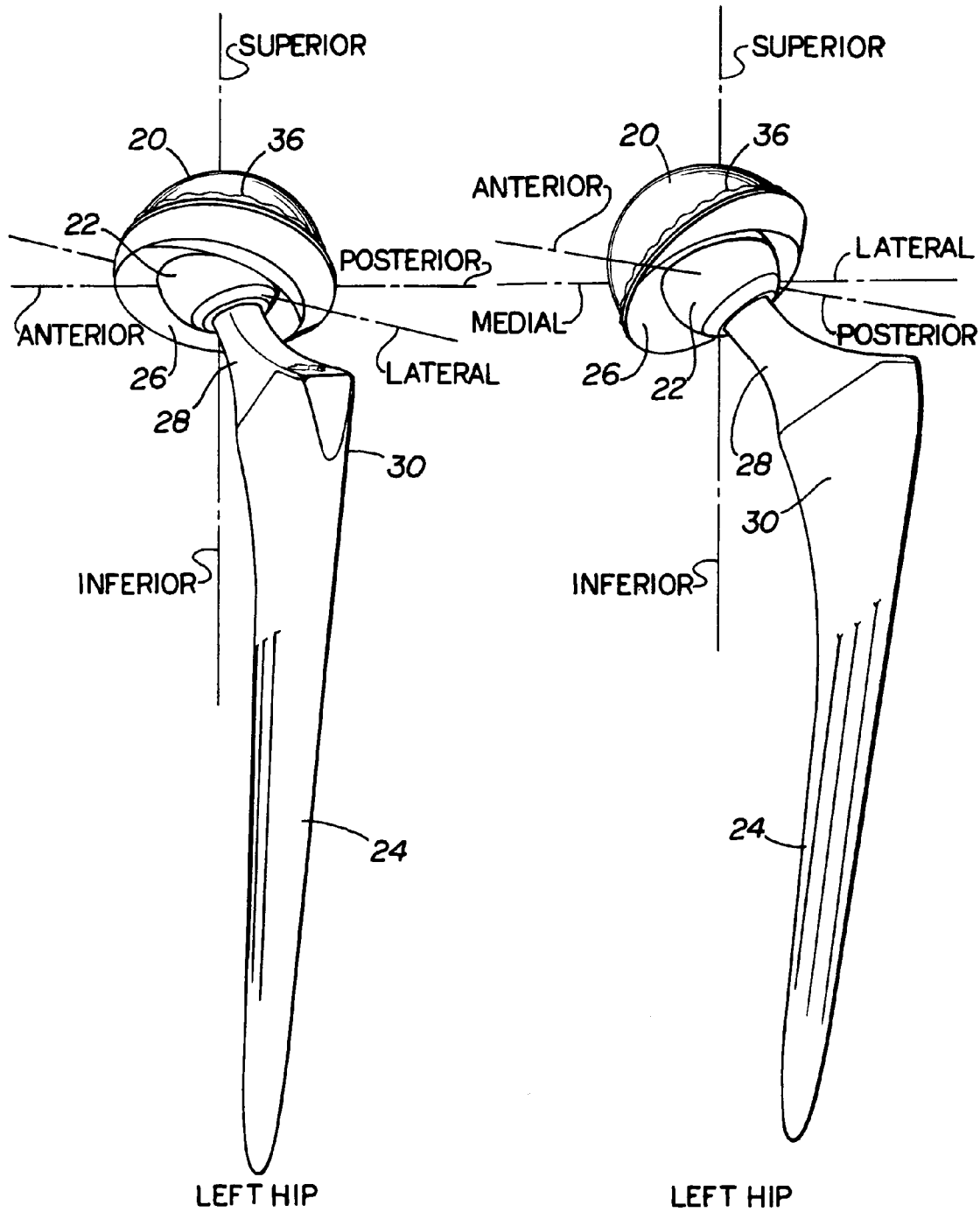
FIGS. 3 and 4 are perspective views of a femoral component and acetabular shell liner of a hip prosthesis for a left hip according to an embodiment of the invention.
Figures 5, 6:
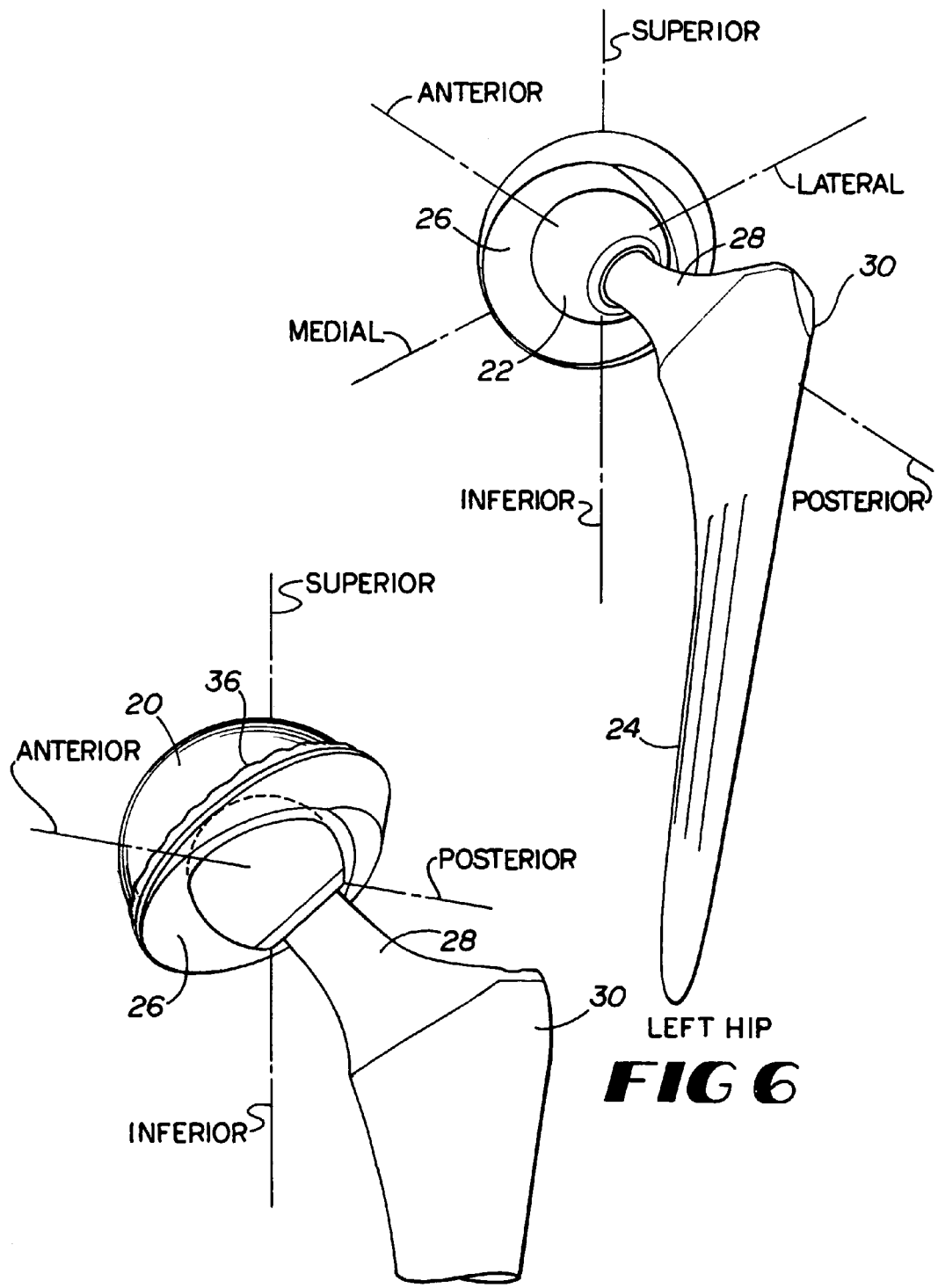
FIG. 5 is a partial view of the femoral component and acetabular shell liner of FIG. 4.
FIG. 6 is a perspective view of a femoral component and acetabular shell liner of a hip prosthesis for a left hip according to an embodiment of the invention.

Methods and structures according to this invention seek to improve the range of motion of the femoral component of a hip prosthesis by varying the rim surface geometry of the rim of an acetabular shell liner in which the femoral component articulates. Varying the geometry of the rim surface relative to the internal concave surface opening or axis of the liner at different areas on the liner allows for optimization of the rim surface geometry, thus providing an increased range of motion. A variable geometry rim surface liner according to this invention has an overall range of motion generally at least comparable to a conventional constant geometry rim surface liner.

Optimization of the acetabular shell liner rim surface geometry requires consideration of many elements in the design of the liner, including, but not limited to, range of motion of the femoral component, mechanical integrity, locking strength between the liner and the shell, material thickness constraints, as well as other considerations. All of these factors must be balanced in designing an optimized acetabular liner, including the variable geometry rim surface. Thus, changing the geometry of a liner to obtain the best possible range of motion is impacted by other design constraints.

The rim, or impingement surface, is the surface of the liner that restricts the rotation of the femoral component. One example of a possible rim surface geometry is a chamfer. One reason a chamfer, curve, or other rim surface, is used is so that if subluxation occurs, the rim surface serves as a guide to aid in hip reduction, or proper relocation.

A liner according to the present invention has an internal concave surface adapted to receive the head of a femoral component, an external surface positioned on an opposing side of the liner from the internal concave surface, and a sculpted surface generally defining at least part of the rim of the liner and which varies around the rim of the liner.

As used herein the term "internal concave surface" refers to the internal concave surface of the liner which receives a femoral component head. The internal concave surface may be hemispherical, oval, elliptical, oblong, or any other generally concave geometric shape. The term "internal diameter" refers to the internal concave surface of a liner; it may be partially spherical, and it may be hemispherical or less than hemispherical. "External diameter" refers to an external surface opposing the internal concave surface which is adapted to be received in an acetabular shell or directly into the acetabulum of a patient. The term "articulation bearing surface" refers to the surface of the internal concave surface in which the head of the femoral component articulates or moves in a manner corresponding to motion of the femur relative to the acetabulum.

The term "rim" or "rim surface", as used herein, refers to a surface of the liner located generally between the internal concave surface and an external surface of the liner, at least portions of which restrict the rotation of the femoral component within the internal concave surface of the liner. "Sculpted surface" means a surface which forms at least part of the rim of the liner and which varies around the rim of the liner according to the orientation of the femoral component in an impingement condition with the rim of the liner and according to other structural and mechanical variables.

One method according to this invention seeks to determine orientation of a femoral component in an impingement condition to the liner rim geometry in order to optimize the maximum range of motion. As an example, one method according to the invention, which may be performed manually or with the aid of a computer, is described below.

1. Provide an acetabular shell liner and a femoral component comprising a head, neck and stem. Preferably, provide an acetabular shell, liner and femoral component. Alternatively, introduce data corresponding to a three dimensional model of a liner and femoral component into computer containing a processing functionality, storage functionality, and rendering functionality. More preferably, introduce information corresponding to the acetabular shell, liner, and femoral component.

2. From an anatomic neutral position, rotate the femoral component within the internal concave surface of the liner to define a radial location on the rim of the liner where the femoral component contacts, i.e. impinges, the rim of the liner. If using a computer, the computer models and/or simulates the configuration of the shell, liner and femoral component and simulates the rotation of the femoral component until the femoral component impinges the rim of the liner at a defined radial location.

3. With the femoral component in this position, note the radial location and define the impingement angle of the femoral component in that position at that radial location on the rim.

4. Record the structure and orientation of this angle at this radial location. Define the location and desired shape of a cross-sectional rim segment at this impingement angle and radial location, based at least in part on the cross-sectional shape of the femoral component where it impinges the rim at this radial location, and note this desired shape.

5. Rotate the femoral component within the liner to define a separate radial location on the rim of the liner where the femoral component impinges on the rim. In the computer example, the computer simulates the movement of the femoral component and may record the radial location.

6. Repeat steps three through five for a desired number of radial locations around the rim. In the computer simulation, the computer may track the data corresponding to the impingement angles and cross-sectional shape of the femoral component in an impingement condition with the liner at each of a plurality of radial locations around the rim.

Figure 14A:
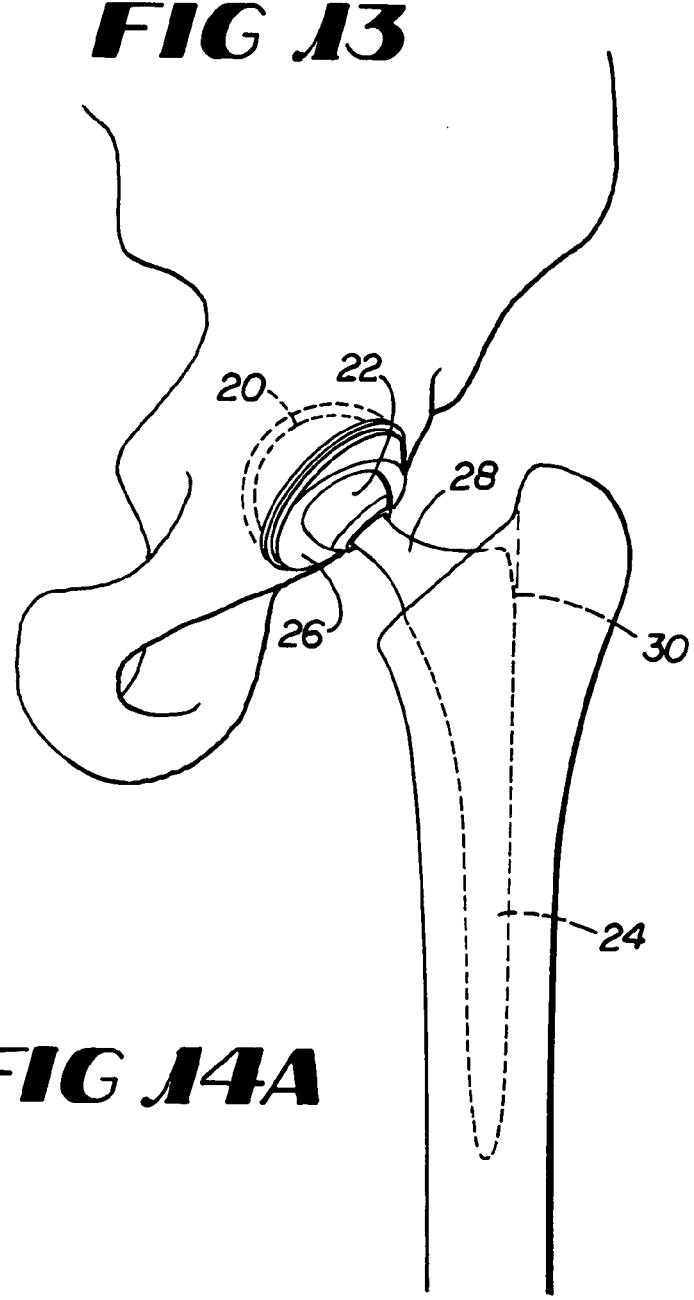
FIG. 14A is a diagram showing the arrangement of an acetabular shell, shell liner and femoral component within a human pelvis.
Figure 14B:
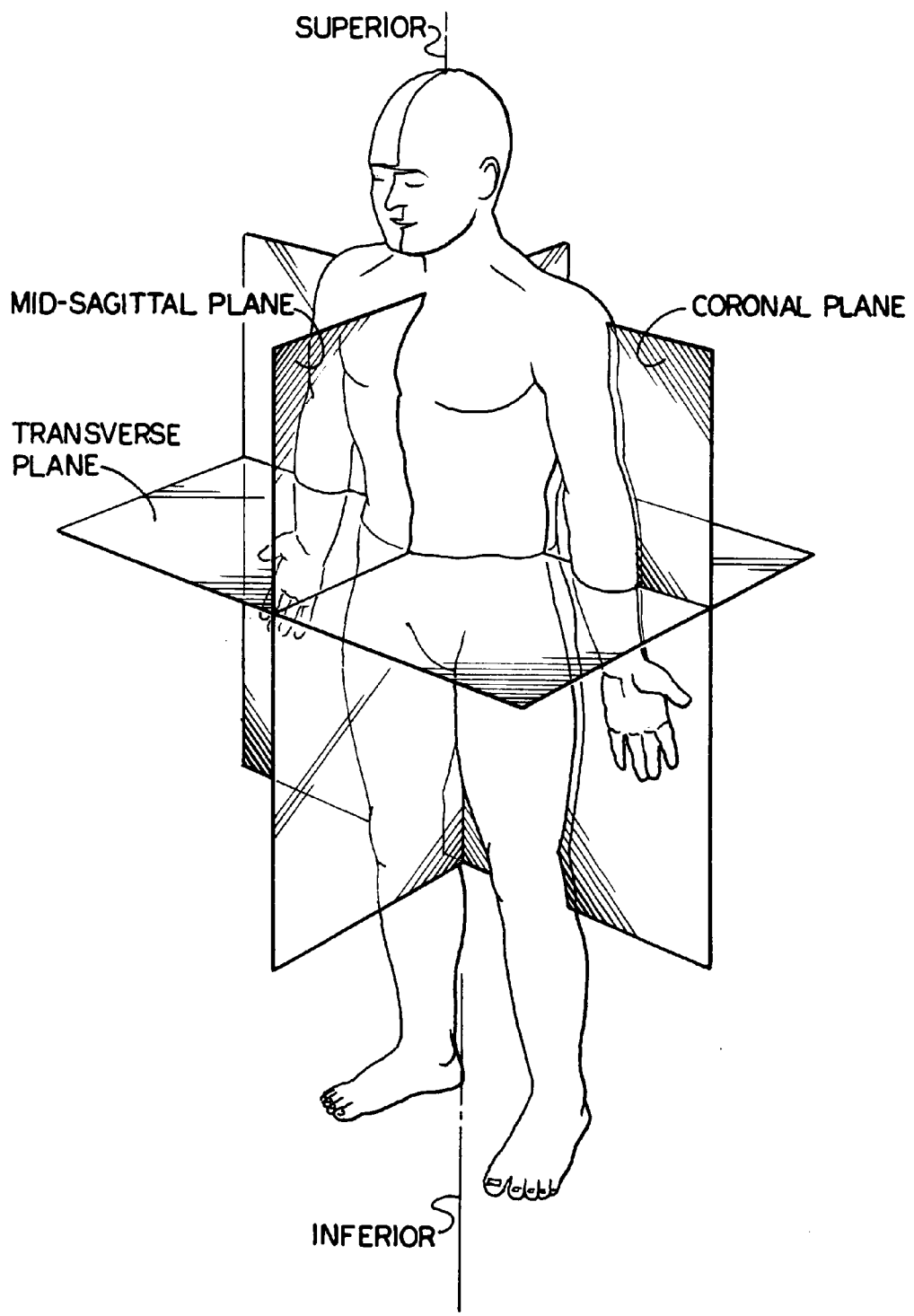
FIG. 14B is a diagram showing coronal, saggital and transverse planes of the body.

In one example rotate, or simulate the rotation of, the femoral component within the liner relative to a relevant anatomical axis of the body. Preferably, rotate the femoral component relative to anatomically relevant axes running through the center of rotation of a femoral component articulating within the internal concave surface of the liner, and oriented in a plane substantially parallel to transverse, coronal or saggital planes of the body. These planes are shown in FIG. 14B. More preferably, rotate or simulate the rotation of the femoral component about axes that are fifteen degrees apart in said planes.

7. Repeat, if desired, steps 1–6, with different femoral component head offsets possible in the assembly of the stem and head to obtain a range of impingement angles and a cross-sectional envelope determined by the group of impingement angles and cross-sectional shapes corresponding to the plurality of femoral components used. Preferably, repeat steps 1–6 with any other structural variations in a set of stem, shell, and liner products or liners.

8. Form the liner with the variable geometry rim surface using the data obtained in steps 1–6, or through step 7 if desired, and form the liner such that the shape of the liner rim varies at a plurality of radial locations in a manner corresponding to the cross-sectional shape of the femoral components in an impingement condition with the liner.

The geometry of the rim surface may be defined in part by using some or all of these data relating to the specified impingement angles and cross-sectional envelopes determined in steps 3–6. It may also, and in some cases additionally, be defined by specifying the rim surface geometry of the liner to be formed by doing necessary or desired extrapolation, interpolation, or estimation based on the impingement angles and locational data from steps 3–6. In the computer simulation example, the computer may define the geometry of the rim based at least in part on the impingement angles, cross-sectional envelope, and locational data obtained in the steps outlined above or on extrapolation, interpolation or estimation therefrom. The computer may produce a set of specifications based on the data obtained in the steps above for forming a liner with a variable geometry rim surface.

All of these steps are subject to the design goals of creating a rim surface optimized for range of motion of the femoral component relative to the liner. More preferably, all of these steps are subject to taking into account other anatomical, performance, durability and structural criteria.

Figure 12:
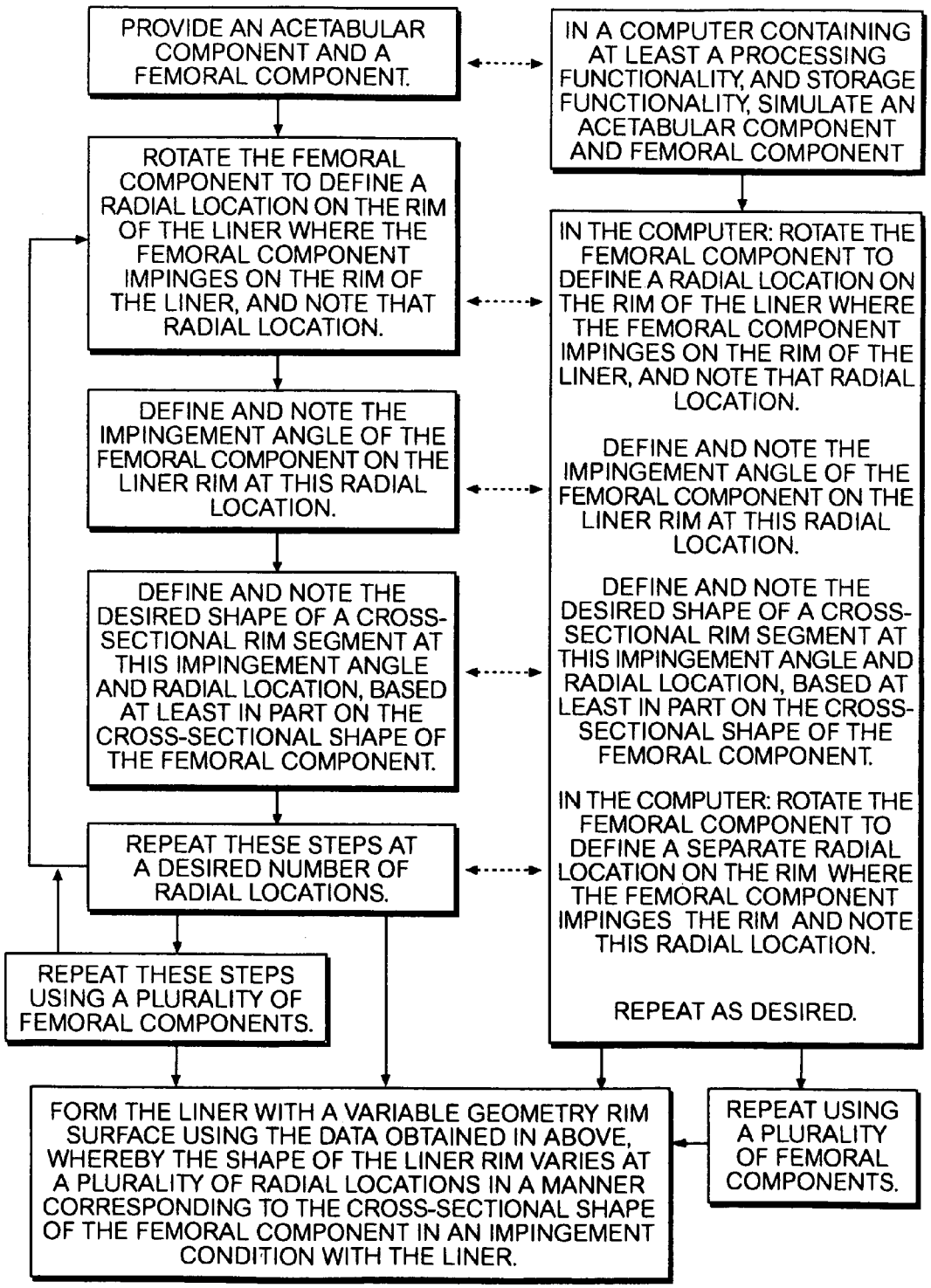
FIG. 12 is a flow chart outlining the steps for making the variable geometry rim surface liner.
Figure 13:
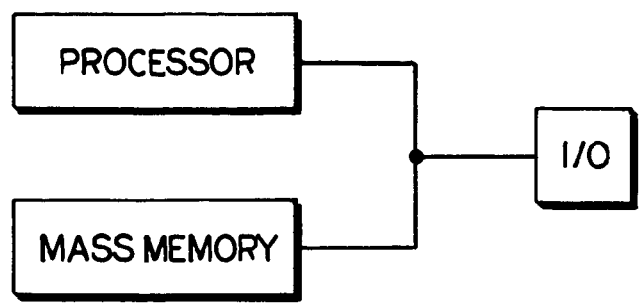
FIG. 13 is a functional block diagram of a system in which the method of FIG. 12 may be performed.

FIG. 12 shows a functional block diagram illustrating the process described above for making the variable geometry rim surface liner of the present invention. The manual method is outlined on the left side of the flow chart, while the right side outlines the computer simulation example. FIG. 13 shows a functional block diagram which represents a hardware environment, or system, in which the simulation method of the present invention may be performed. The system illustrated comprises a processor capacity, a mass memory capacity, and an input/output capacity. Any or all functionalities represented in this diagram may be implemented or reside on one or more "computers," processors, platforms, networks or other systems.

In a particular example, the liner shown in FIGS. 1–9 was made using Unigraphics® software, running on a Windows NT® operating system on a personal computer with a Pentium II® processor. Steps 1–6 outlined above were performed on Unigraphics® brand computer aided design package which used the data to produce an image of a three-dimensional solid model liner with a variable chamfer rim geometry. Any device design software or software which can be used to design objects, running on any desired platform using any operating system, whether or not network based, can be used in accordance with the present invention. Also produced was a code corresponding to the specification of this liner which was used to program a machine tool, such as a 5-axis CNC milling machine, to form the liner. The liners of the present invention may be formed of various materials, including but not limited to ceramic, polyethylene, ultra high molecular weight polyethylene, and highly cross-linked ultra high molecular weight polyethylene, more preferably ultra high molecular weight polyethylene.

The liners of the present invention are typically used in combination with a metallic shell. However, the liners may also be implanted directly into the acetabulum of a patient. When implanted directly into the acetabulum, the liners are generally secured into the acetabulum with bone cement. The liners also may be mechanically fixed within the acetabulum by bone screws or screw threads on the external surface of the liner. Another method of securing the liner in the acetabulum is by providing a bone in-growth surface which is integral to the external surface of the liner. This surface may be molded into or otherwise integral to the external surface of the liner. This integral bone in-growth surface may be made by creating a roughened area on the external surface of the liner. This integral bone in-growth surface may also comprise a textured matrix which is incorporated into the material of the external surface of the liner; such a matrix may include metal porous beads, fiber mesh, or other surfaces which provide a scaffold into which the patient's bone will grow, thereby physically securing the liner within the acetabulum.

The geometry of the rim surface specified according to the method of this invention is preferably a chamfered surface connecting at least part of the internal concave surface of the liner and an external surface of the liner. Structures according to this invention include a family of variable geometry rim surface acetabular liners having differing sizes, with each size having different rim surface geometries.

As one example of the present invention, consider generally hemispherically shaped liners whose internal diameters are 28 mm to fit a common size head of a femoral implant. These liners include a chamfer as the rim surface. Each of the outer diameters of the liners get progressively larger with each increasing size, corresponding to the size of the acetabulum. As the size increases, the rim surface angle, or chamfer angle, can widen, or become more obtuse as a general matter. In this particular example, the center axes of the internal diameters of the liners are oriented, or anteverted, at 20 degrees relative to the central axis of the shell, or other surface in which the liner is adapted to be received. In other words, the opening of the liner is at 20 degrees to the opening of the shell. In another example, the center axes of the internal diameters of the liners may be anteverted up to about 45 degrees relative to the central axis of the shell. The center axis of the liner internal diameter may be shifted relative to the center axis of the shell in any direction, in an anteverted liner, the axis is oriented toward the anterior of the body.

FIGS. 1 to 9 show an example of these types of liners. As shown in FIGS. 1 and 3 to 7, acetabular shell liner 20 is adapted to receive head 22 of femoral component 24. Liner 20 has variable angle chamfer 26, which chamfer angle 27 ($\phi$) varies in order to optimize the range of motion of femoral component 24 with respect to other structural variables. In these figures the chamfer angle, 27 is defined as the angle at any point on or near the periphery of the liner internal diameter at which the surface of the chamfer is positioned relative to the center axis of the opening of the internal diameter of the liner, about which the stem articulates. However, the angle may also be defined relative to any reference line or plane defined by the structure of the liner, such as the center axis or an axis of rotation of the inner diameter, the center axis or axis of rotation of the external, or outer, diameter, or some other reference entity. FIG. 2A shows a perspective view of a liner having variable chamfer, angle 27. Variable angle 27 is shown in cross-section in FIG. 2B, and the mapping of the angle variation is depicted in FIG. 2C.

As shown in FIGS. 1 and 3 to 7, head 22 and liner 20 act as a ball and socket joint. The contact during articulation of the femoral component neck 28 with liner 20 is minimized by varying the impingement angle 27 of chamfer 26 to allow neck 28 a broader range of motion prior to contact with liner 20. In this example, neck 28 of stem 30 has a circulotrapezoidal (such as a rounded, generally rectangular) cross-section. As the femoral component 24 is rotated, the periphery of the neck 28 limits the rotation of the stem 30 relative to the liner 20 because contact of the neck 28 with the chamfer 26 stops rotation of the femoral component.

As follows from the method described above, at the points where the neck 28 is more likely to contact the outer edge of the chamfer 26, the angle 27 is made more obtuse in order to produce a condition where the femoral neck contacts the inner and outer edges of the chamfer at the same time, thus allowing a broader range of motion. Where the neck 28 is likely to contact only the inner edge, the angle 27 is made more acute to produce a condition where the femoral neck contacts the inner and outer edges of the chamfer at the same time. According to the method described above, the condition of contact in which the neck will require the widest chamfer angle is isolated, resulting in a chamfer angle that is customized for the neck geometry of the femoral component.

In another embodiment, the variable angle 27 of liner 20 is made to correspond to any shaped stem neck so that the varying angle 27 is optimized for a neck with a particular geometry, such as cylindrical. Different liner rim surface geometries may be used depending upon the particular neck geometry.

As shown in FIGS. 1 and 3 to 7, in this example, the center of rotation of the internal diameter in liner 20 is lateralized, or shifted laterally, by 4 mm. In another embodiment, a variable geometry rim surface is used with a nonlateralized liner, with a liner lateralized by up to 8 mm, with a liner lateralized up to 10 mm, or with a liner that is lateralized differently. As used herein and as understood by those of skill in the art, "lateralized" refers to a liner wherein the center of the internal concave surface, or internal diameter, has been shifted laterally, or laterally and somewhat inferiorly, with respect to how the liner is oriented in a patient. In another embodiment, a variable geometry rim surface is used with a liner wherein the center of the internal concave surface, or internal diameter, has been shifted medially by up to 4 mm or up to 8 mm.

FIG. 10 graphically illustrates the comparison of range of motion of a variable angle chamfer acetabular shell liner according to this invention, the liner shown in FIGS. 1–9, and range of motion of a prior art liner with a constant chamfer angle of 147°. Both liners have a 28 mm internal diameter, and in both liners the center of the internal diameter is lateralized by 4 mm and the opening of the internal diameter is anteverted by 20°. The femoral component used with both liners was a size 14 Smith & Nephew Synergy® Stem, measuring 160 mm in length and with a 28 mm diameter head.

The solid line curve shown in FIG. 10 illustrates an example of a range of motion envelope that was derived using the above described method for varying the rim surface geometry. This range of motion was characterized by components of flexion-extension and abduction-adduction. The dotted line is an example of a range of motion envelope provided by a non-variable, i.e. constant, geometry rim surface liner. On this graph the zero point, or anatomically neutral point, represents a liner oriented at 45° of abduction and 20° of anteversion and a femoral component oriented at 7° of adduction and 20° of anteversion. From this point the femoral component is rotated, as in a patient after implantation, about various anatomically relevant axes located, in this case, 15 degrees apart in a transverse plane of the body, to define the limit of range of motion, or impingement angle, about each axis.

This can be demonstrated by placing FIG. 10 face-up on the floor with the flexion axis pointed forward, i.e. anteriorly, and standing above it with the left foot positioned on top of the graph and aligned with the flexion/extension axis. Rotating the left leg forward, in flexion, the limit of motion to liner rim impingement is approximately 118° with the variable angle chamfer liner, but only about 113° with the prior art constant angle chamfer liner. Rotating the leg backwards about the same axis, in extension, the limit of motion to liner rim contact is about 38° with the variable chamfer angle liner and about 36° with the prior art constant angle chamfer liner. This procedure was repeated, rotating a femoral component about axes located 15 degrees apart, thereby generating a range of motion envelope for both the variable angle chamfer liner and prior art constant angle chamfer liner shown by the solid and dotted line curves, respectively. As can be seen, the range of motion provided by the liner according to the present invention is superior.

In the example shown in FIGS. 1 and 3 to 9, liner 20 has a serrated edge 36 in order to interface with the acetabular shell. Each spline angle of serration is 15 degrees, thus, the liner can be oriented at 15 degrees all around and locked in place in an acetabular shell. Other types of interface with an acetabular shell may also be employed.

Figure 11A:
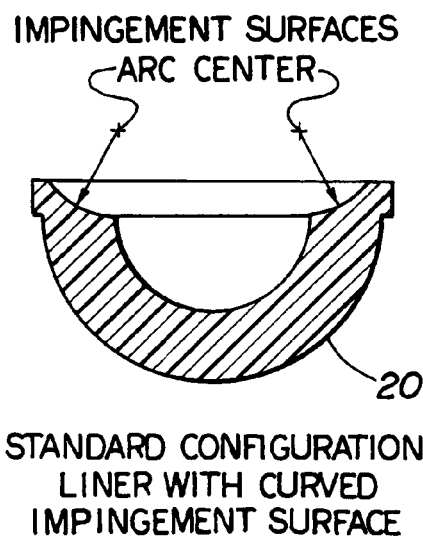
FIG. 11A is a cross-sectional view of an acetabular liner having a concave rim surface.
Figure 11B:
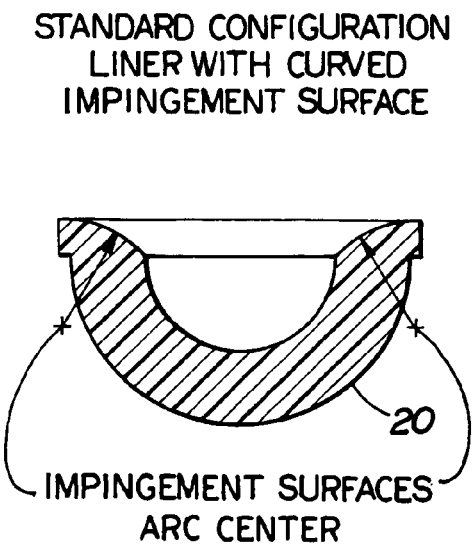
FIG. 11B is a cross-sectional view of an acetabular liner having a convex rim surface.

As described in the example above, the rim surface is a chamfer. Another example is a concave rim surface on a liner, as shown in FIG. 11A. In this embodiment, the liner fits with a stem that has a convex neck. A variable geometry rim surface according to this invention may be employed on this liner. In this example, the radius of curvature of the surface, or the center of curvature, varies relative to the internal diameter of the liner in order to optimize range of motion with respect to other structural variables, rather than varying the angle of the rim surface as with a chamfer. Other interface surfaces may also be optimized to obtain the maximum desired range of motion, such as a convex rim surface liner, shown in FIG. 11B.

Figure 11C:
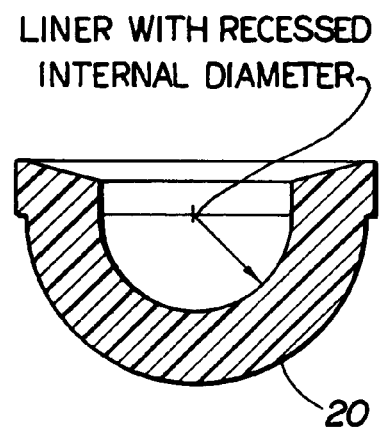
FIG. 11C is a cross-sectional view of an acetabular liner having a recessed internal diameter.
Figure 11D:
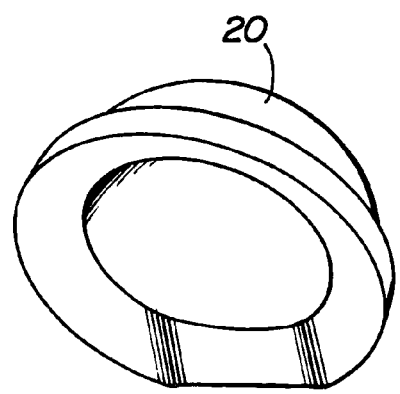
FIG. 11D is a cross-sectional view of an acetabular liner having a "cut out" or recessed rim segment.

A variable geometry rim surface according to this invention may be employed with many types of acetabular shell liners. For example, in one embodiment, a variable geometry rim surface is used with a 0 degree liner. The variable geometry rim surface may be applied to a liner which is anteverted, as shown in the figures, or with a liner that is not anteverted. In another embodiment, a variable geometry rim surface is applied to an acetabular shell liner with a less than 180 degree capture angle, i.e. a liner that provides less than 180 degrees of coverage of a femoral head adapted to be received in the internal concave surface of the liner. The invention can also be used with a liner that has a recessed radial segment, or lip, that dips below 180 degrees of coverage, as shown in FIG. 11D. The variable geometry rim surface can also be applied to a high-wall liner, which is a liner with a raised radial segment, also called a lip or shoulder, which extends above 180 degrees of coverage.

One alternative embodiment of this invention involves the use of a variable geometry rim surface in a constrained liner. A constrained liner is one that has greater than hemispherical coverage around the head such that the head is constrained within the internal diameter, thus preventing subluxation and dislocation. While use of a constrained liner is generally not desirable due to resulting decreased range of motion, it is necessary in some patients who are repetitive dislocators.

The variable geometry rim surface may also be employed in a liner with a sunken, or recessed, internal concave surface. A recessed internal concave surface liner is similar to a constrained liner in that it provides greater coverage of the femoral component head to reduce the risk of dislocation. In the recessed liners the center of the internal concave surface is recessed to sink the articulation bearing surface of the internal concave surface deeper into the liner, creating a surface between the articulation bearing surface of the internal concave surface and the rim of the liner, which serves to reduce dislocation. In recessed liners with a hemispherical internal concave surface, the hemispherical portion of the internal diameter is sunken into the liner, creating a recessed, cylindrical shaped, area near the opening of the internal diameter where the sides of the internal diameter extend substantially straight in the direction of the opening, rather than continuing to curve around the femoral component head. Such a liner is depicted in FIG. 11C.

Another embodiment of the invention is a divided rim surface in which the rim surface of the liner is divided into several constant angle sections so as to approximate a single varying angle rim surface. In another embodiment, the geometry of the rim surface varies around the rim of the liner and is symmetric about a plane, i.e. the reflection about the plane is a mirror image.

The foregoing description of the preferred embodiments of the invention has been presented only for the purpose of illustration and description and is not intended to be exhaustive or to limit the invention to the precise forms disclosed. Many modifications and variations are possible in light of the above teaching. The embodiments were chosen and described in order to explain the principles of the invention and their practical application so as to enable others skilled in the art to utilize the invention and various embodiments and with various modifications as are suited to the particular use contemplated.

What is claimed is:

1. A prosthetic device comprising:
   (a) an acetabular shell comprising an internal concave surface adapted to receive a liner and an external surface adapted to be received in an acetabulum; and
   (b) an acetabular liner having:
      an internal concave surface adapted to receive the head of a femoral component, the concave surface having a periphery with an opening defined by an internal diameter and having a central axis;
      an external surface positioned on an opposing side of the liner from the internal concave surface and adapted to be received in the internal concave surface of the acetabular shell; and
      a rim located between the internal concave surface and the external surface of the liner, at least a portion of the rim comprising a variable angle chamfer surface comprising a plurality of variable angles, each variable angle defined as the angle at any point on or near the periphery of the liner internal diameter at which the surface of the chamfer is positioned relative to the center axis of the opening of the internal diameter of the liner.

2. A device according to claim 1, wherein the central axis of the liner is an axis substantially perpendicular to the center axis of the internal concave surface of the liner.

3. A device according to claim 1, wherein the central axis of the liner is an axis defined by the external surface of the liner.

4. A device according to claim 1, wherein the variable angle chamfer varies according to angles measured at a plurality of radial locations around the rim relative to the central axis of the liner.

5. A device according to claim 1, wherein the plurality of variable angles define impingement angles of a femoral component that includes a head adapted to be received in the internal concave surface of the liner and wherein the impingement angles are disposed to permit an increased range of motion at a corresponding radial location on the rim.

6. A device according to claim 1, wherein the plurality of variable angles are determined using a group of impingement angles corresponding to a plurality of femoral components in an impingement condition with the liner whose heads are adapted to be received in the internal concave surface of the liner.

7. A device according to claim 1, wherein the shape of the variable angle chamfer surface varies according to the cross-sectional shape of a portion of a femoral component that is in an impingement condition with the liner.

8. A device according to claim 1, wherein the variable angle chamfer is symmetric about a plane.

9. A device according to claim 1, wherein a distance across the opening of the internal concave surface of the liner is from about 22 mm to about 36 mm.

10. A device according to claim 1, wherein the external surface of the liner is adapted to be received in an acetabular shell with an external diameter of about 40 mm to about 80 mm.

11. A device according to claim 1, wherein the liner further includes a locking surface for securing the liner in the acetabular shell.

12. A device according to claim 11, wherein the locking surface comprises a serrated edge.

13. A device according to claim 1, further including a shoulder on the liner.

14. A device according to claim 1, wherein the shell has a center and the central axis of the liner internal concave surface is offset from the center of the shell.

15. A device according to claim 14, wherein the center of the liner internal concave surface is shifted laterally by up to about 10 mm.

16. A device according to claim 14, wherein the center of the liner internal concave surface is shifted laterally by about 4 mm.

17. A device according to claim 14, wherein the center of the liner internal concave surface is shifted medially by up to about 8 mm.

18. A device according to claim 1, wherein the opening of the liner internal concave surface is anteverted.

19. A device according to claim 18, wherein the shell has a center and the central axis of the liner internal concave surface is anteverted up to about 45 degrees relative to the central axis of the shell.

20. A device according to claim 18, wherein the shell has a center and the central axis of the liner internal concave surface is anteverted about 20 degrees relative to the central axis of the shell.

21. A device according to claim 1, where the shell has a center and the central axis of the liner internal concave surface is oriented up to about 45 degrees relative to the central axis of the shell.

22. A device according to claim 1, where the shell has a center and the central axis of the liner internal concave surface is oriented about 20 degrees relative to the central axis of the shell.

23. A device according to claim 1, further comprising a surface located between the liner internal concave surface and the rim surface, which serves to reduce dislocation of a femoral component received within the liner.

24. A device according to claim 1, wherein the liner internal concave surface is an internal diameter.

25. A device according to claim 1, wherein the liner internal concave surface is generally hemispherical.

26. A device according to claim 1, further comprising a femoral component comprising a head, neck and stem, wherein the head is adapted to articulate within the internal concave surface of the liner.

* * * * *